United States Patent
Meece et al.

(10) Patent No.: US 6,849,324 B2
(45) Date of Patent: Feb. 1, 2005

(54) UNDIRECTIONALLY COLD STRETCHED NONWOVEN WEBS OF MULTIPOLYMER FIBERS FOR STRETCH FABRICS AND DISPOSABLE ABSORBENT ARTICLES CONTAINING THEM

(75) Inventors: Barry DeWayne Meece, Pelzer, SC (US); Thomas Edward Quantrille, Simpsonville, SC (US)

(73) Assignee: BBA Nonwovens Simpsonville, Inc., Simpsonville, SC (US)

(*) Notice: Subject to any disclaimer, the term of this patent is extended or adjusted under 35 U.S.C. 154(b) by 26 days.

(21) Appl. No.: 09/949,108

(22) Filed: Sep. 6, 2001

(65) Prior Publication Data

US 2002/0039637 A1 Apr. 4, 2002

Related U.S. Application Data (63) Continuation of application No. 09/187,677, filed on Nov. 6, 1998, now abandoned.

(51) Int. Cl.[7] .................................................. B32B 5/26
(52) U.S. Cl. .................. 428/195; 428/198; 442/328; 442/329; 442/361; 442/366; 442/409; 442/411
(58) Field of Search ................................ 428/195, 198; 442/328, 329, 361, 366, 409, 411

(56) References Cited

U.S. PATENT DOCUMENTS

| | | |
|---|---|---|
| 3,952,073 A | 4/1976 | Isaka et al. |
| 3,969,562 A | 7/1976 | Suzuki |
| 4,048,364 A | 9/1977 | Harding et al. |
| 4,116,892 A | 9/1978 | Schwarz |
| 4,153,664 A | 5/1979 | Sabee |
| 4,153,751 A | 5/1979 | Schwarz |
| 4,223,063 A | 9/1980 | Sabee |
| 4,285,100 A | 8/1981 | Schwarz |
| 4,289,832 A | 9/1981 | Schwarz |
| 4,293,608 A | 10/1981 | Isaka et al. |
| 4,343,852 A | 8/1982 | Isaka et al. |
| 4,621,119 A | 11/1986 | Lu |
| 4,908,253 A | 3/1990 | Rasmussen |
| 4,981,747 A | 1/1991 | Morman |
| 5,108,827 A | 4/1992 | Gessner |
| 5,114,781 A | 5/1992 | Morman |
| 5,208,098 A | 5/1993 | Stover |
| 5,238,733 A | 8/1993 | Joseph et al. |
| 5,242,436 A | 9/1993 | Weil et al. |
| 5,244,482 A | 9/1993 | Hassenboehler, Jr. et al. |
| 5,296,289 A | 3/1994 | Collins |
| 5,422,172 A | 6/1995 | Wu |
| 5,683,787 A | 11/1997 | Boich et al. |
| 5,804,286 A * | 9/1998 | Quantrille et al. .......... 428/198 |
| 5,851,935 A | 12/1998 | Srinivasan et al. |

FOREIGN PATENT DOCUMENTS

| | | |
|---|---|---|
| EP | 0127483 | 12/1984 |
| EP | 0685586 A | 12/1995 |
| WO | WO 96/16216 | 5/1996 |

* cited by examiner

*Primary Examiner*—Elizabeth M. Cole
(74) *Attorney, Agent, or Firm*—Alston & Bird LLP (57) ABSTRACT

A nonwoven web of multipolymer fibers is described that is unidirectionally stretched and permanently elongated at ambient conditions and exhibits a substantial increase in tensile strength in the stretch direction. The ratio of tensile strength of the web in the direction of fiber orientation to the tensile strength in the other direction is at least about 10:1. The ratio of elongation at peak load in a direction transverse to the direction of fiber orientation is at least about 6:1. The multipolymer fibers normally are a blend of polyethylene and a polypropylene homopolymer or copolymer, one of which is a dominant phase and one of which is a dispersed phase. A third component having elastomeric properties that is at least partially miscible with one or both of the other components is included in some blends. The nonwoven webs are stretchable well beyond their initial dimensions in the direction perpendicular to the stretch direction and are especially useful in laminates with elastomeric members for use in disposable absorbent articles to impart elasticity thereto.

20 Claims, 9 Drawing Sheets

_Fig.1._

_Fig.2._

UNDIRECTIONALLY COLD STRETCHED NONWOVEN WEBS OF MULTIPOLYMER FIBERS FOR STRETCH FABRICS AND DISPOSABLE ABSORBENT ARTICLES CONTAINING THEM

CROSS REFERENCE TO RELATED APPLICATIONS

This application is a continuation of application Ser. No. 09/187,677 filed Nov. 6, 1998 now abandoned.

FIELD OF THE INVENTION

The invention relates to elasticized composite fabrics for use in disposable absorbent articles and to the components of these fabrics.

BACKGROUND OF THE INVENTION

Disposable diapers are composite absorbent articles that are designed to be worn about the lower torso as undergarments by incontinent persons and by infants and young children prior to toilet training. Disposable diapers typically include a liquid impervious back sheet as the outer surface of the diaper, a liquid pervious topsheet as the inner surface of the diaper for placing adjacent the skin of the wearer, and an absorbent core placed between the topsheet and the back sheet for absorbing urine and other liquids. The absorbent core is normally contained in a central, longitudinally extending region of the diaper and the topsheet and back sheet are normally bonded about the periphery of the diaper.

The diaper is placed between the legs with the topsheet next to the skin and the ends are fastened at the waist to hold the diaper in place for the collection and retention of urine and feces. One area of concern in the development and construction of the modern disposable diaper has been maintaining the wearer's comfort and the fit of the diaper throughout the period of use of the diaper, especially on active infants and young children.

Disposable diapers have front and back waist regions that are usually characterized by side panels or ear flaps that extend in the lateral direction on each end of the diaper so as to encircle the waist and hold the diaper in place. The front waist region normally includes a landing member upon which decorative indicia may be placed. The back waist region normally includes a securing tab on each side for attaching to the landing member. The securing tab and landing member can be attached by hook and prong fastening means similar to Velcro, by a pressure-sensitive adhesive on a securing tab tape, or by other suitable means.

Disposable diapers may also include elasticized waist bands, leg cuffs and side panels. The elasticized components improve the fit of the diaper and can assist in precluding leakage from the diaper.

U.S. Pat. No. 5,242,436 is directed to a disposable diaper that has an elasticized waist band with a dual tensioning fastening system to improve the dynamic fit of the elasticized waist band and the containment characteristics of the absorbent article. A pair of elasticized side panels that are elastically extensible in the lateral direction are disposed in the back waist region between the topsheet and the back sheet in the ear flaps of the diaper on either side of the absorbent core.

The topsheet and the backsheet are extensible, but inelastic. The webs can be stretched, but are permanently elongated and do not have significant recovery of their pre-stretched dimension. It is necessary to activate the topsheet and back sheet in the region of the elastic side panels so that the topsheet and back sheet can stretch and recover with the side panels. The topsheet and back sheet are activated by incremental mechanical stretching in the cross-machine direction. A laminate of the topsheet, back sheet, and elastic side panel is passed in an untensioned condition through at least one set of meshing corrugated rolls. The laminate is rendered elastically extensible in the cross direction up to the limit of incremental stretching.

U.S. Pat. Nos. 4,981,747 and 5,114,781 are directed to the preparation of composite elastic laminates for use in disposable absorbent articles, including diapers. The laminates are of elastic materials and extendable but nonelastic nonwoven webs. The webs are described as "reversibly necked," which is to say that the webs are permanently elongated in one direction and necked down in a direction generally perpendicular to the direction of elongation of the web. The web is heat treated while necked. The heat treatment is said to impart memory to the nonelastic webs so that the webs can then be stretched and recover in a direction generally parallel to the direction of neckdown and perpendicular to the direction of elongation. Extension of the reversibly necked material is described as limited to the pre-necked dimensions.

A composite elastic laminate can be prepared by laminating the reversibly necked material to an elastic material. The laminate is said to be elastic in a direction generally parallel to the direction of neckdown of the reversibly necked material. A laminate that is elastic in two directions can be prepared if the reversibly necked material is laminated to an elastic material elongated in the direction of extension of the web and then relaxed. The reversibly necked material is gathered between points of attachment to the elastic material and is said to have stretch and recovery to the extent the gathers allow the elastic material to elongate.

Hassenboehler, Jr. et al. U.S. Pat. No. 5,244,482 describes another method for drawing a web of nonelastic nonwoven fibers in the machine direction. The stretched web is said to be useful as a filter material and to have reduced pore size, improved uniformity in pore size, and high lateral elasticity characteristic of stretch fabric having approximately 120% elongation to break. The web is said to be useful in preparing laminates with webs of elastomeric polymers, among others.

The precursor web has substantial bonding and relatively low processing extensibility and is heated to its softening temperature and drawn in the machine direction. Elastomeric polymer webs and webs having 50% standardized elongation before break are said to be totally unsatisfactory for use in the practice of method.

It would be desirable to provide alternative composite elastic laminates that have improved properties, are more versatile, or require less effort to prepare. It would be desirable to develop nonwoven webs for composite elastic laminates that are strong enough to withstand the rigors of incremental mechanical stretching in diaper construction where it is desirable to use elastomeric strands or scrim for breathability, rather than films.

SUMMARY OF THE INVENTION

The invention provides a nonwoven web of multipolymer fibers, a method for making the web, a composite elastic laminate that includes the web and an elastic component, and a disposable absorbent article that includes the composite elastic laminate of the invention. The laminate is suitable for use in disposable absorbent articles, including use as elasticized side panels in diapers that are subjected to incremental mechanical stretching to activate the topsheet and the back sheet. The laminate is also suitable for use as a discrete stretchable member that is attached to the side edges of the main body of a garment, including a diaper, and has exceptional cloth like hand.

The nonwoven web is made from multipolymer fibers that are substantially oriented in one direction. A plurality of discrete bond sites throughout the web bond the fibers together. The ratio of the tensile strength of the web in the direction of orientation of the fibers to the tensile strength of the web in the other direction is at least about 10:1.

The multipolymer fibers are highly elongatable. The web can be stretched to orient the fibers in one or the other of the machine direction or the cross machine direction to substantially increase the elongation of the web at peak load in a direction perpendicular to the elongation of the web and to also increase the tensile strength in the web in the direction of elongation. The web can be stretched in the absence of heat treatment, which is to say that the web can be stretched at a temperature from about 35 to 150 degrees Fahrenheit. Normally, the web will be stretched at an ambient temperature from about 65 to 110 degrees Fahrenheit.

Prior to stretching, the web will typically have an elongation at peak load in at least one of the machine direction or the cross machine direction of at least 70 percent. Mechanical stretching permanently elongates the web and develops a high degree of stretchability in the direction perpendicular to the elongation of the web. The elongation at peak load in the direction perpendicular to the direction of stretch is increased by a factor of at least about 2:1, and in a more specific aspect of the invention, by a factor of more than 4:1. Composite elastic fabrics made with the nonwoven web of the invention can typically be stretched to the elastic limit of the elastic component since the web is usually capable of stretching farther. The web is substantially strengthened and does not undergo thinning and damage during incremental mechanical stretching.

The multipolymer fibers can be formed with the different polymers in discrete structural domains or from a blend of polymers that are miscible, immiscible, or a blend of miscible and immiscible polymers. A blend can also be used as one component in a multipolymer fiber formed of discrete structural domains. In one embodiment, the polymers are immiscible and are blended to form a dominant continuous phase and at least one dispersed phase. Exemplary immiscible polymers include polyethylene, including linear low density polyethylene and polypropylene. These polymers are normally considered to be inelastic. Either polymer can be the dominant continuous phase. The blend can also include an elastic component. The preferred blend includes a third component that is at least partially miscible with the two phases and gives the blend highly elongatable characteristics.

An example of a suitable blend for forming multipolymer fibers is:

isotactic polypropylene present in an amount of about 65 to 80 percent by weight based upon the weight of the blend;
  linear low density polyethylene present in an amount from about 1 to 5 percent by weight based upon the weight of the blend; and
  a block or grafted polyolefin copolymer or terpolymer having at least a portion of the chain thereof miscible with the isotactic polypropylene and wherein the block or grafted polyolefin copolymer or terpolymer is present in an amount from about 15 to 30 percent by weight based upon the weight of the blend.

Examples of such a block or grafted polyolefin copolymer are the commercially available Catalloy™ copolymers available from Montell.

The multipolymer fibers can be spunbond continuous filaments, carded discontinuous staple fibers and meltblown fibers. Normally, the web will be prepared from continuous spunbond filaments.

In another embodiment, the invention comprises a composite fabric that has at least one layer of an elastomeric component bonded to at least one layer of the nonwoven web described above. The elastomeric component can be selected from elastic strands, scrim, elastic films, and breathable elastic films. The fabric can be gathered in the direction in which the nonwoven web component previously was permanently elongated by mounting the web to the stretched elastic component and then relaxing the elastic component in the manner taught in U.S. Pat. No. 5,114,781.

In yet another embodiment, the invention comprises a method for substantially increasing the elongation at peak load of a bonded nonwoven web wherein a web of multipolymer fibers is prepared and then stretched in one of the machine or cross machine directions at a temperature from about 35 to 150 degrees Fahrenheit to permanently elongate the web. The elongation at peak load of the web in the direction perpendicular to the stretch direction is substantially increased. The method can include the additional step, if desired, of stabilizing the web against retraction of the fibers by lightly bonding the stretched web, normally through the application of heat and pressure.

Thus, the invention provides a composite elastic fabric with cloth like hand and good cover characteristics that is suitable for use in disposable absorbent articles, especially as elastic side panels in diapers, either as discrete members attached to the main body of the garment or in laminates mounted between the topsheet and back sheet. The nonwoven web component of the composite fabric has the strength to perform well in incremental stretching. The web can be permanently elongated in one direction to impart substantial ability to stretch in a direction perpendicular to the direction of elongation, all in the absence of heat treatment.

BRIEF DESCRIPTION OF THE DRAWINGS

Some of the objects and advantages of the invention have been stated. Others will appear when taken in connection with the accompanying drawings and photomicrographs, in which.

DETAILED DESCRIPTION OF THE INVENTION

The invention will be described with particular reference to the drawings, in which illustrative embodiments of the invention are set forth. It should be understood that persons skilled in the art to which this invention pertains may modify the specific details described while still continuing to use the invention. The description should be understood as a broad teaching of the invention that is directed to the persons of skill in the applicable arts.

Figure 1:
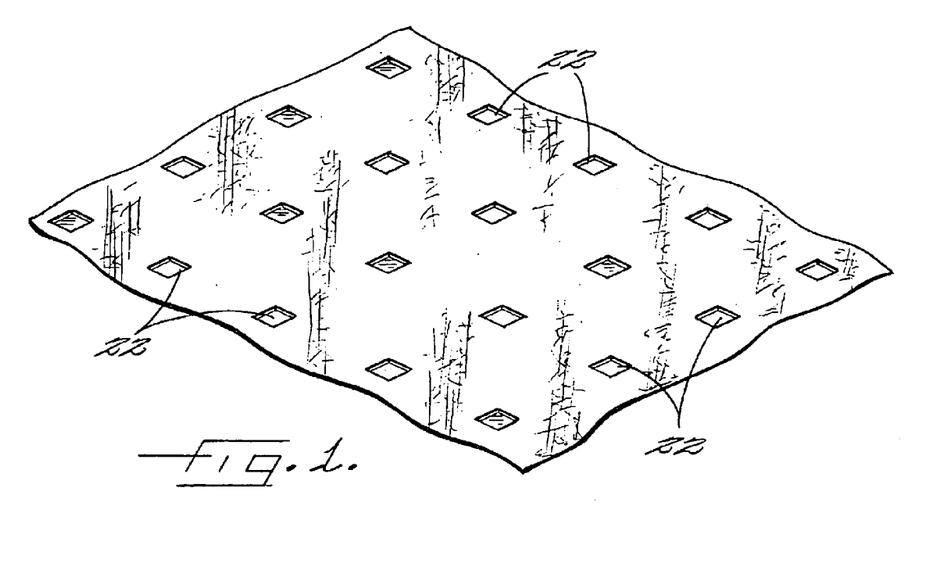
FIG. 1 is a perspective view of a portion of a bonded nonwoven web of multipolymer fibers prior to stretching in accordance with the invention.

FIG. 1 is a perspective view of a portion of a bonded nonwoven web 20 prepared from multipolymer fibers. The nonwoven fibrous web represented in FIG. 1 should be considered in a generic sense to include generally planar structures that are relatively flat, flexible and porous and are comprised of multipolymer staple fibers or continuous filaments. The nonwovens may be carded, spunbonded, wet laid, air laid or meltblown. Normally, prior to stretching, the web will have an elongation at peak load in at least one of the machine direction or the cross machine direction of at least 70 percent. In the embodiment illustrated, the nonwoven fibrous web is a spunbonded nonwoven comprising multipolymer spunbond continuous filaments. The filaments are bonded together at discrete bond sites 22 distributed throughout the fabric to form a unitary, coherent nonwoven web.

Figure 8:
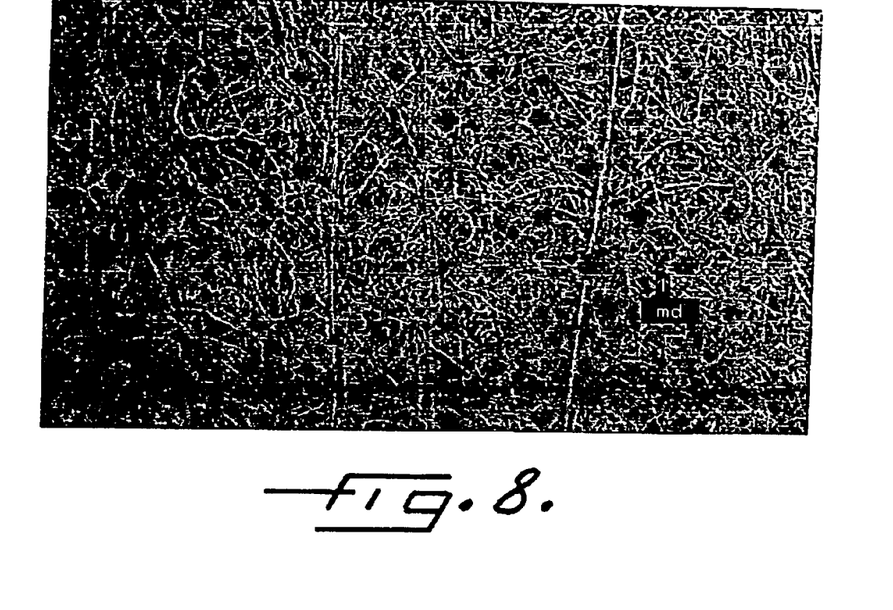
FIG. 8 is a photomicrograph at 5× magnification of a pointbonded spunbond nonwoven web of multipolymer continuous filaments prior to stretching in accordance with the invention.
Figure 9:
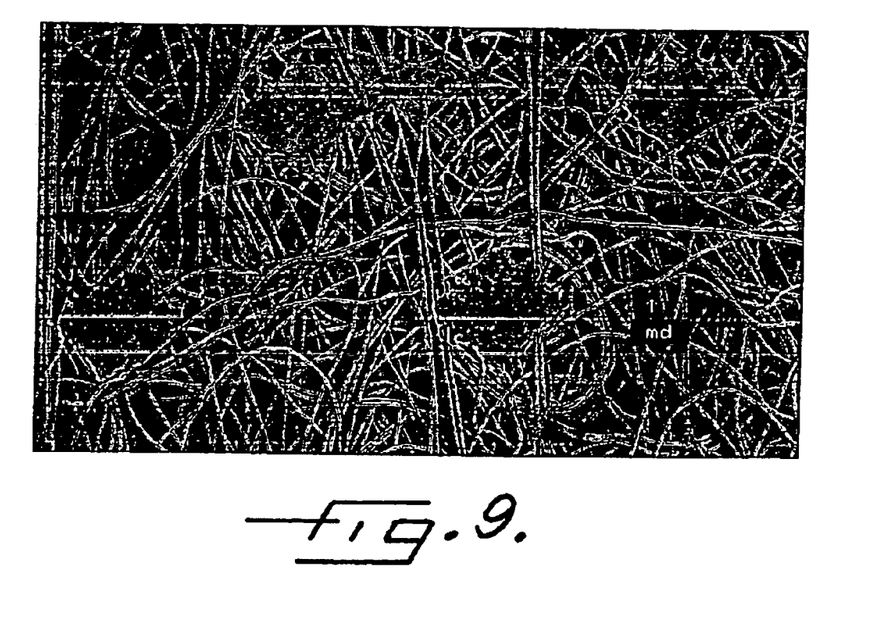
FIG. 9 is a photomicrograph showing the web of FIG. 8 at 20× magnification.

FIG. 8 is a photomicrograph at 5× magnification showing a point bonded nonwoven fabric of spunbond continuous multipolymer filaments. This same web is shown in FIG. 9 at a magnification of 20 times. The individual filaments and the consolidated areas of the point bonds are evident. As is evident from the photomicrographs, the point bonds are planar and lie in the plane of the web. The point bond sites 22 comprise discrete areas where the filaments have been fusion bonded by the application of heat and pressure. In the embodiment illustrated, the bond sites 22 are point bonds, but other known configurations or shapes could be employed, including lines or other patterns.

The multipolymer fibers of the invention are predominantly formed from polymers that normally are considered nonelastic. Useful polymer combinations for use in the practice of the invention are taught in published PCT International Patent Application WO 96/16216 entitled Extensible Composite Nonwoven Fabrics. The contents of this application and the teachings contained therein are hereby incorporated by reference in their entirety. The term "multipolymer fibers" includes staple and continuous filaments prepared from blends of two or more polymers and from two or more polymers present in discrete structural domains in the fiber. For the purposes of the invention, the term "polymer" is used in a general sense, and is intended to include homopolymers, copolymers, grafted copolymers, and terpolymers. The term blend is also used generally herein, and is intended to include immiscible and miscible polymer blends. The polymers are considered to be "immiscible" if they exist in separate, distinct phases in the molten state; all other blends are considered to be "miscible." It is understood that varying levels of miscibility can exist, and are also intended to be within the scope of this invention.

Blends with more than two polymers may also be utilized, including those with three or more polymer components. Both immiscible and miscible polymers may be added to a two component blend to impart additional properties or benefits with respect to blend compatibility, viscosity, polymer crystallinity or phase domain size.

Since the polymers employed in the invention will undergo extrusion, stabilizers and antioxidants are conventionally added to the polymer. Other additives may also be added in accordance with the present invention. For example inorganic additives such as titanium dioxide, talc, fumed silica or carbon black. The polymer resin may also contain other additives, such as other polymers, diluents, compatibilizers, antiblocking agents, impact modifiers, plasticizers, UV stabilizers, pigments, delusterants, lubricants, wetting agents, antistatic agents, nucleating agents, rheology modifiers, water and alcohol repellents, and the like. It is also anticipated that additive materials which have an affect on processing or product properties, such as extrusion, quenching, drawing, laydown, static and/or electrical properties, bonding, wetting properties or repellency properties may also be used in combination with the blend. In particular, polymeric additives may also be used that impart specific benefits to either processing and/or end use.

The multipolymer fibers are normally formed of a polymer blend composed of two or more polymers. The polymers of the blend can be miscible, immiscible, or a combination of miscible and immiscible polymers. In one embodiment in accordance with the invention, the polymers may exist as a dominant continuous phase and at least one substantially discontinuous dispersed phase. In the case where the blend exists as a dominant continuous phase and at least one discontinuous phase, other polymers may also be present which are either miscible in one, or the other, or both polymer phases.

According to a further aspect of the invention, the multipolymer fibers are formed of a polymer blend including a relatively low modulus polymer and at least one higher modulus polymer. It is believed that this combination is particularly valuable when the low modulus polymer is the dominant phase and the higher modulus polymer is dispersed therein. It is theorized that the higher modulus polymer acts to "reinforce" the low modulus dominant phase, lending stability to spinning, and stiffening the web just enough to allow for higher bond temperatures while reducing the risk of the web sticking to and wrapping the calender. In the case of multipolymer fibers formed of an immiscible polymer blend it is believed that the small amount of the dispersed polymer may have the effect of wind up speed suppression (WUSS) on the dominant polymer phase as described by Brody in U.S. Pat. No. 4,518,744. Wind up speed suppression occurs when a small amount of an immiscible additive effectively reduces the degree of molecular orientation within the fiber at a given filament spinning velocity. The result is a filament with generally higher elongation and lower tenacity.

In yet another aspect of the invention, the multipolymer fibers are formed of a polymer blend composed of a dominant continuous phase, and at least one polymer, having low mutual affinity with the dominant phase, dispersed therein, and at least one additional polymer which is at least partially miscible in one or the other or both continuous and dispersed polymer phases. If the one additional polymer is miscible in the dominant phase, and effectively reduces its crystallinity, it is believed that the improved extensibility observed in the resulting composites may be due to an "impact-modifying" effect. If the one additional polymer has an affinity for both polymers, or serves to lower the surface energies between the two phases, it is believed that the improvement observed in the composite extensibility is due to a compatibilization effect. Independent of theory, the blend must ultimately form filaments or fibers, which when formed into webs and composite structures exhibit the properties described by the invention, meaning low fuzz and good elongation.

In one embodiment, the multipolymer fibers may comprise from 1 to 50 percent by weight polyethylene and from 99 to 50 percent by weight polypropylene. Fabrics formed from such blends exhibit low fuzz and good elongation.

In applications where tensile strength is particularly important and high elasticity is of lesser concern, the composite fabric may include a coherent, extensible nonwoven web formed of fibers of a polyethylene and polypropylene blend where the polyethylene is present in the range of 1% to 10% and the polypropylene is present in the range of 90% to 99% by weight. In still another embodiment, very substantial and surprising increases in elongation can be achieved by blending a third polymer component into the blend. For example, the multipolymer fibers may include a dominant amount of a polypropylene, such as isotactic polypropylene, a small amount of a polymer having low mutual affinity with the dominant polymer, such as polyethylene, and an additional third polymer which either reduces crystallinity and/or compatibilizes the blend. What results is a softer web, with extremely high extensibility. Preferred multipolymer fibers according to this embodiment may comprise greater than 50 percent by weight polypropylene, 1 to 10 percent polyethylene, and 10 to 40 percent of the third polymer. Suitable additional third polymers include polypropylene copolymers and terpolymers such as the commercially available CatalloyΘ copolymers available from Montell. These resins are characterized by having the comonomer(s) exist to some degree in blocks, and wherein at least some portion of the polymer chain is miscible with one or the other, or both, dominant and dispersed polymer phases. Other suitable polymers are the ReflexΘ flexible polyolefins from Rexene. These crystallinity reducing resins are characterized as having atactic segments present in the polymer chain, such that the "tacticity" of the polymer is affected.

Especially preferred multipolymer fibers according to this embodiment comprise 65 to 80 percent isotactic polypropylene, 1 to 5 percent polyethylene, and 15 to 30 percent of a polyolefin copolymer wherein at least a portion of the chain is miscible with isotactic polypropylene.

Another class of useful and advantageous products according to this aspect of the invention employ multipolymer fibers formed of a polymer blend comprised of a soft, extensible polymer phase, and at least one additional polymer having low mutual affinity with the soft, extensible phase, such that it modifies either the Theological, mechanical, and/or thermal properties of the fibers in a way that improves processability (e.g. melt spinning), bonding and/or abrasion resistance while maintaining high extensibility. In a preferred embodiment the soft, extensible phase is present as a dominant, continuous phase. For example, polyethylene can be used as the soft, extensible dominant phase and a polypropylene as the additional modifying polymer. In a preferred embodiment the additional polymer is added in a small proportion relative to the dominant phase. In another preferred embodiment, the additional polymer exhibits higher viscosity relative to the dominant phase. Blending a relatively small proportion of the higher viscosity polypropylene with the soft, extensible polyethylene imparts greatly increased abrasion resistance to a nonwoven fabric formed from the polymer blend, without significant adverse effect upon other important fabric properties, such as extensibility, softness, tensile strength, etc. The spinnability of the polyethylene is also improved by the presence of the additional polypropylene. According to this embodiment, the fibers preferably comprise between 2 to 50 percent by weight of the propylene polymer, e.g. 3% ethylene-propylene copolymer, and 98 to 50 percent by weight of the soft, extensible polymer, e.g. polyethylene. In one particularly preferred embodiment, the fiber composition may range from 5 to 40 percent by weight propylene polymer, and most desirably between 5 to 25 percent by weight propylene polymer and 75 to 95 percent by weight polyethylene. Especially suited for applications requiring good extensibility, tensile strength and abrasion resistance are fiber compositions of from 5 to 25 percent by weight propylene polymer. A most preferred embodiment contains 5 to 25 percent by weight of ethylene-propylene copolymer or terpolymer and 75 to 95 percent by weight linear low density polyethylene. In these embodiments, the lower melting polyethylene is present as a substantially continuous phase in the blend and the higher melting propylene polymer is present as a discontinuous phase dispersed in the polyethylene phase.

In producing the fibers, the polyethylene and polypropylene components are combined in appropriate proportional amounts and intimately blended before being melt-spun. In some cases sufficient mixing of the polymer components may be achieved in the extruder as the polymers are converted to the molten state. In other cases, more dynamic mixing may be required.

Various types of polyethylene may be employed. As an example, a branched (i.e., non-linear) low density polyethylene or a linear low density polyethylene (LLDPE) can be utilized and produced from any of the well known processes, including metallocene and Ziegler-Natta catalyst systems. LLDPE is typically produced by a catalytic solution or fluid bed process under conditions established in the art. The resulting polymers are characterized by an essentially linear backbone. Density is controlled by the level of comonomer incorporated into the otherwise linear polymer backbone. Various alpha-olefins are typically copolymerized with ethylene in producing LLDPE. The alpha-olefins which preferably have four to eight carbon atoms, are present in the polymer in an amount up to about 10 percent by weight. The most typical comonomers are butene, hexene, 4-methyl-1-pentene, and octene. In general, LLDPE can be produced such that various density and melt index properties are obtained which make the polymer well suited for melt-spinning with polypropylene. In particular, preferred density values range from 0.87 to 0.95 g/cc (ASTM D-792) and melt index values usually range from 0.1 to about 150 g/10 min. (ASTM D1238-89, 190EC). Preferably, the LLDPE should have a melt index of greater than 10, and more preferably 15 or greater for spunbonded filaments. Particularly preferred are LLDPE polymers having a density of 0.90 to 0.945 g/cc and a melt index of greater than 25. Examples of suitable commercially available linear low density polyethylene polymers include those available from Dow Chemical Company, such as ASPUN Type 6811 (27 MI, density 0.923), Dow LLDPE 2500 (55 MI, 0.923 density), Dow LLDPE Type 6808A (36 MI, 0.940 density), and the Exact series of linear low density polyethylene polymers from Exxon Chemical Company, such as Exact 2003 (31 MI, density 0.921).

Various polypropylenes made by processes known to the skilled artisan may also be employed. In general, the polypropylene component can be an isotactic or syndiotactic propylene homopolymer, copolymer, or terpolymer. Examples of commercially available propylene homopolymers which can be used in the present invention include SOLTEX Type 3907 (35 MFR, CR grade), HIMONT Grade X10054-12-1 (65 MFR), Exxon Type 3445 (35 MFR), Exxon Type 3635 (35 MFR) AMOCO Type 10-7956F (35 MFR), and Aristech CP 350 J (melt flow rate approximately 35). Examples of commercially available copolymers of propylene include Exxon 9355 which is a random propylene copolymer with 3% ethylene, 35 melt flow rate; Rexene 13S10A, a 10 melt flow rate random propylene copolymer with 3% ethylene; Fina 7525MZ, an 11 melt flow rate 3% ethylene random propylene copolymer, Montel EPIX 30F, a 1.7% ethylene, 8 melt flow rate random copolymer of propylene. When the propylene polymer is the dominant continuous phase of the blend, the preferred melt flow rate is greater than 20. When the propylene polymer exists as the dispersed phase of the blend, the preferred melt flow rate is less than 15 and most preferably less than 10.

In still another embodiment, the multipolymer fibers of the web may be bicomponent or multicomponent fibers or filaments. The term bicomponent or multicomponent refers to the existence of the polymer phases in discrete structured domains, as opposed to blends where the domains tend to be dispersed, random or unstructured. The polymer components can be configured into any number of configurations including sheath-core, side-by-side, segmented pie, islands-in-the-sea, or tipped multilobal. A coherent extensible nonwoven web can be made, for example, from a sheath-core bicomponent fiber having a polyester core and a polyethylene sheath, or the sheath or core can comprise a blend as discussed above. Alternatively, the extensible web can comprise a single web containing a combination of spunbonded filament and meltblown fibers or a combination of carded staple fibers and meltblown fibers.

The extensible nonwoven web, in all embodiments in accordance with the present invention, is characterized by having high surface abrasion resistance and high elongation. The surface abrasion resistance of the web may be conveniently measured objectively by physical tests which are standard in the industry, such as the Taber abrasion test as defined by ASTM Test Method D-3884-80. Extensible webs useful in the composite fabrics of the present invention are characterized by having a Taber abrasion value (rubber wheel) of greater than 10 cycles. The webs are further characterized by having an elongation at peak load (ASTM D-1682), prior to stretching, in either the machine direction (MD) or in the cross-machine direction (CD) or both of at least 70 percent, more preferably at least 100 percent, and most desirably at least 150 percent. The multipolymer fibers of the web are of relatively fine diameter, typically 10 denier or less.

The web shown in FIG. 1 has been bonded so that it can be stretched, but has not yet been stretched. The web shown in FIG. 1 has been point bonded by passing the web through a calender nip in which one of the calender rolls is smooth and one of the calender rolls has a patterned surface for applying the bonding pattern. Intermittent point bond regions 22 are formed wherein the web is bonded. The discrete bond sites comprise areas where the fibers have been fusion bonded together. It should still be possible to trace an individual filament through the bond site if the bond site is not overbonded. Preferably, the fused regions cover between 6 and 30 percent of the area of the web, more preferably 8 to 20 percent, and most preferably 12 to 18 percent of the web is covered. By bonding the web in accordance with these percentage ranges, the filaments are allowed to elongate throughout the full extent of stretching while the strength and integrity of the fabric is maintained.

The skilled artisan should recognize that there are myriad other ways to bond a web sufficiently to enable the web to be stretched. While thermal point bonding is most preferred for spunbond, carded, and other webs, any thermal, chemical, or mechanical bonding treatment may be used to form a coherent web structure.

Figure 2:
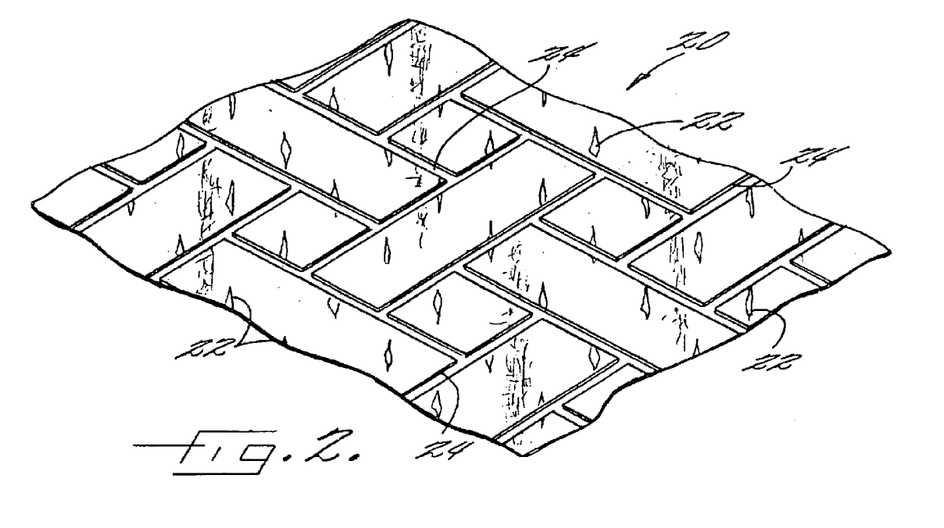
FIG. 2 is a perspective view of the nonwoven web of FIG. 1 after the nonwoven web has been permanently elongated in accordance with the invention and stabilized by application of light bonding.

Turning now to a discussion of the properties of the web after stretching, FIG. 2 represents the nonwoven web 20 of FIG. 1 that has been permanently elongated by mechanical stretching in either the machine direction or the cross direction. It should be understood that the web can be subjected to stretching in either of the cross machine or machine direction to achieve the benefits of the invention, but not both. Normally, the web is stretched in a direction having an elongation at peak load of at least 70 percent. It should be recognized that this property could be met in one of or both the machine and cross machine directions.

The web has been stretched and permanently elongated by the stretching at a temperature of between about 35 to 150 degrees Fahrenheit. The web normally is elongated in the absence of heat treatment at an ambient temperature, which typically varies from about 65 degrees on a relatively cold day to about 110 degrees on a hot summer day, and most typically is on the order of about 65 to 85 degrees.

As a result of the "cold" stretching, the nonwoven web develops extraordinary elongation at peak load in the direction perpendicular to the direction of stretch. Elongation at peak load can be at least about 400 to 500% and values above 700% have been achieved. Typically, the ratio of elongation at peak load in the direction perpendicular to the direction of stretch to the elongation at peak load in the stretch direction is increased at least about 2:1 to more than 10:1. Increase by a factor of at least about 6:1 to 8:1 is typical. Thereafter, the fabric is capable of stretch well beyond the original dimension of the fabric in the direction perpendicular to the stretch direction. The tensile strength of the webs in the direction of orientation of the filaments, which is normally the stretch direction, is greatly increased. The ratio of tensile strength of the web in the direction of orientation of the fibers to the tensile strength of the web in the other direction is at least about 10:1 and can be increased to at least about 16:1.

A further characteristic of the web is high extensibility at low force. The nonwoven web has an elongation in one direction, which is the direction perpendicular to the stretch direction, of at least 70% when a load is applied to the web in that direction that is less than or equal to about 300 grams force per inch. A force of about 300 grams force per inch or less is about the force that the consumer feels on the wrist when using a fabric in accordance with the invention. The web can be prepared wherein the elongation of the web in the direction perpendicular to the stretch direction is at least 100% to 350% at a load of less than 300 grams force per inch. Table 2, below, shows examples at 100%, 200%, and 350% elongation at loads of less than 300 grams force per inch.

Figure 10:
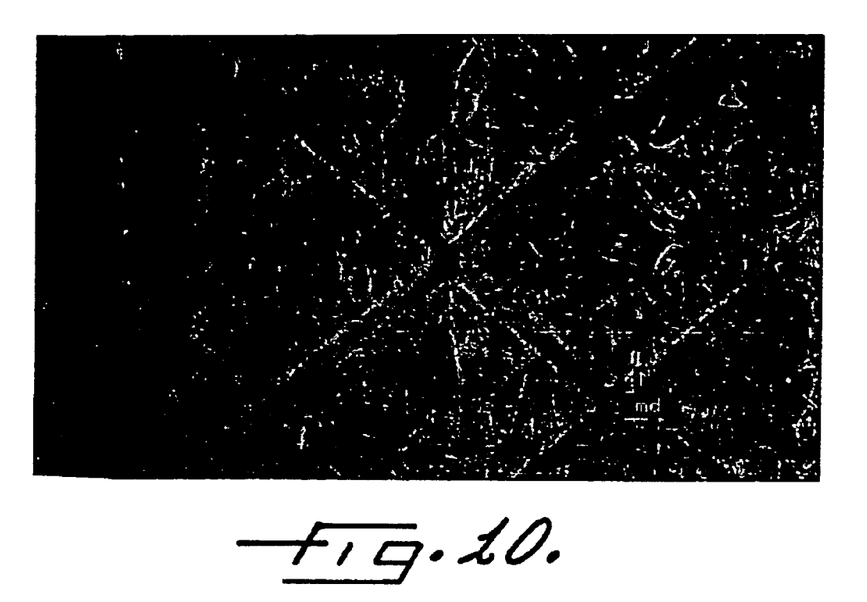
FIG. 10 is a photomicrograph at 5× magnification showing a point bonded spunbond nonwoven web of multipolymer continuous filaments after stretching in the machine direction followed by light bonding to stabilize the stretched web against retraction.
Figure 11:
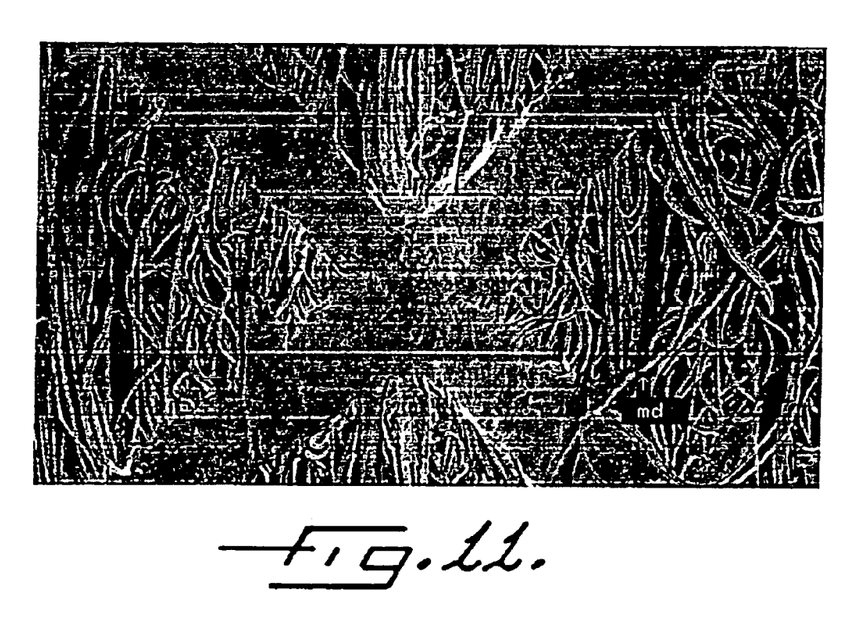
FIG. 11 is a photomicrograph showing the web of FIG. 10 at 20× magnification.

While not wishing to be bound by theory, it is believed that the filaments that are not oriented in the stretch direction prior to stretching become oriented in the stretch direction as a result of the stretching, but are either not elongated or are only partially elongated. This feature is graphically illustrated in the photomicrographs shown in FIGS. 10 and 11, which are at 5 and 10× magnification, respectively, and show a multipolymer continuous filament pointbonded spunbond nonwoven web that has been stretched in the machine direction. A substantial number of the filaments can be seen to be oriented in the machine direction, which is the direction of stretch. In any event, the fabric becomes stretchable in the direction perpendicular to the stretch direction to an extent beyond the prestretched dimension in that direction.

Figure 12:
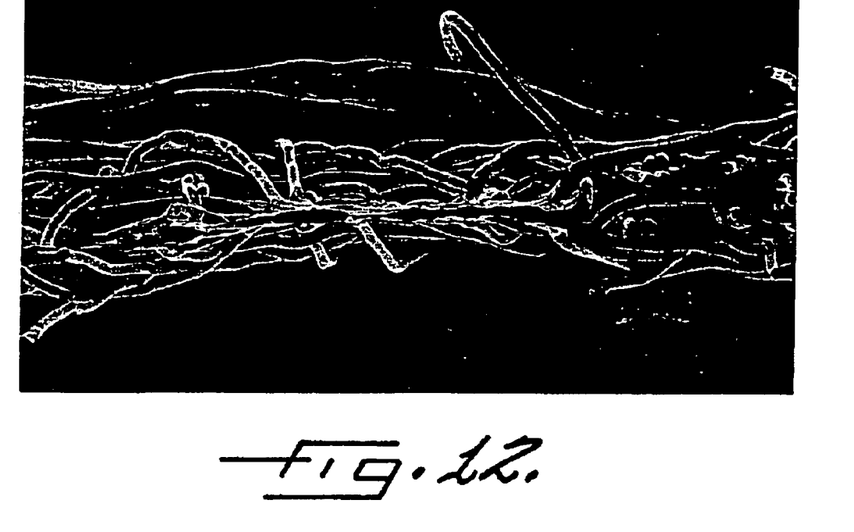
FIG. 12 is a photomicrograph at 20× magnification of a section through a pointbonded spunbond nonwoven web of multipolymer continuous filaments prior to stretching in accordance with the invention and showing a pointbond horizontally oriented in the body of the fabric.
Figure 13:
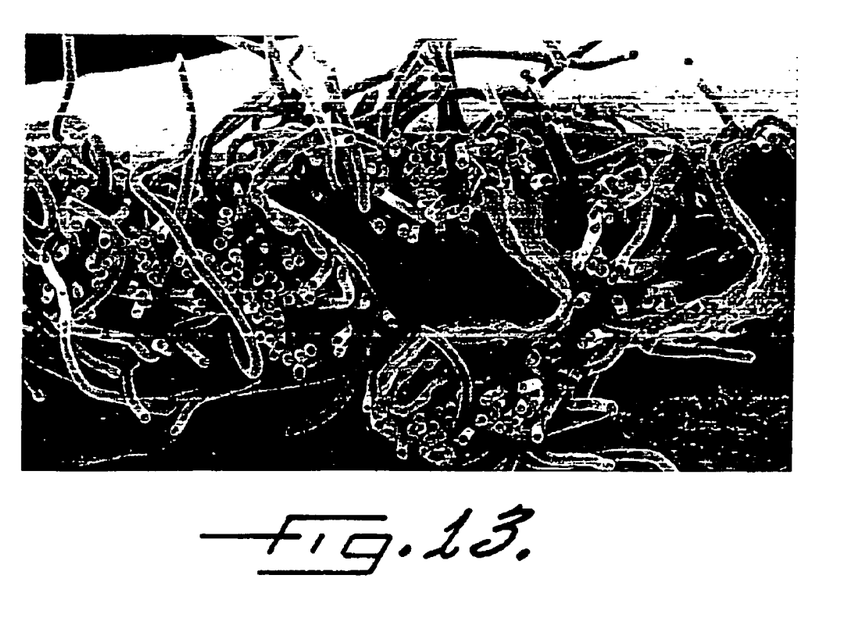
FIG. 13 is a photomicrograph at 20× magnification of a section through a pointbonded spunbond nonwoven web of multipolymer continuous filaments after the web has been stretched in accordance with the invention and showing a pointbond that has become vertically orientated in the fabric as a result of the stretching.

The fabric also develops a z-direction axis and becomes thicker as the fabric is stretched and the dimension in the direction perpendicular to the stretch direction becomes smaller. The point bonds 22, which initially are flat and lie in the plane of the web, become strained, and become oriented generally in the z-axis direction within the thickness dimension of the fabric and disposed between the opposing fabric surfaces. This detail is graphically illustrated in FIG. 13, which shows in a photomicrograph at 20× magnification the distorted, deformed point bonds of a non-planar configuration embedded in the web between opposite surfaces of the web. These bond sites have been pulled into the body of the spunbond nonwoven web and extend in the Z-direction axis. Prior to stretching, the pointbond was horizontally oriented as shown in the photomicrograph of FIG. 12, which is also at 20× magnification. Increase in the thickness of the nonwoven web due to stretching can also be seen by comparing FIGS. 12 and 13.

As shown in FIG. 2, the fabric has been lightly bonded after stretching with a plurality of point bond sites 24 in a pattern reminiscent of cross laid bricks. The point bond sites 24 include film-like fused regions that are generally planar and are parallel to the surface of the web and lie at the web surface. The stretched fabric was bonded by passing through a calender nip at light pressure and low heat to stabilize the web and to substantially preclude retraction, since a small about of elastomeric polymer is used in the fibers of which the fabric is made. The bonding is graphically illustrated in the photomicrographs of FIGS. 10 and 11. It should be recognized that a wide variety of suitable bonding patterns are available and should provide equivalent performance in the practice of the invention. The bonding should be enough to stabilize the web against retraction of the fibers after elongation to the desired extent, but not so great as to preclude stretching in the direction perpendicular to the stretch direction, for which the fabric is designed.

It is usually advisable to lightly bond the web after stretching when the web will be rolled rather than supplied directly to a laminator for lamination with an elastomeric component. The elastomeric component of the web can cause the web to retract in the roll if the web is not lightly bonded.

The fabric illustrated in FIG. 2 can be stretched in any of several ways known to the skilled artisan. The fibers normally are extruded, collected on a web forming surface, bonded, and stretched in line. Alternatively, for certain processes, the nonwoven web is rolled prior to stretching and stretching is accomplished as a separate operation.

Stretching in the cross machine direction normally is accomplished using a standard tenter frame. It should be recognized that other methods and apparatus can be used to stretch the nonwoven web in the cross direction, although not necessarily with equivalent results. For example, the web can be incrementally stretched in the cross direction using intermeshing or interdigitating rollers.

Figure 3:
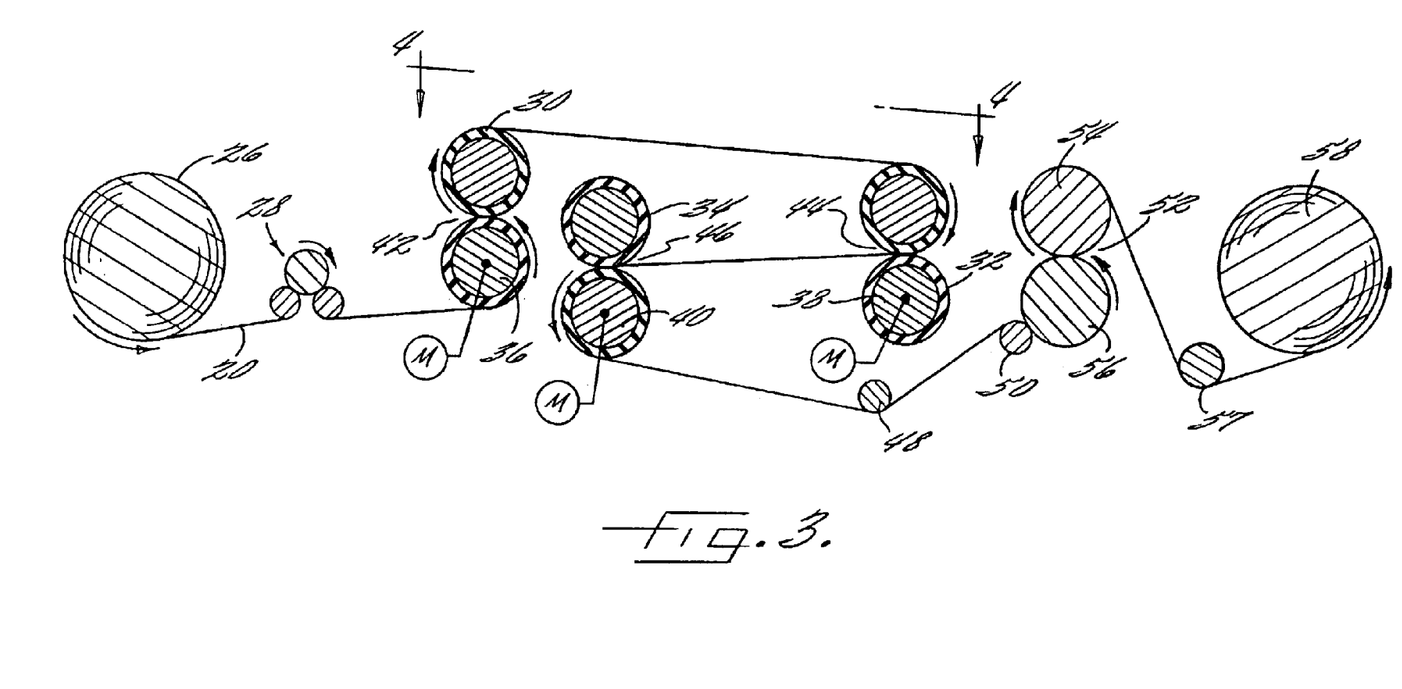
FIG. 3 is a schematic of an exemplary process for permanently elongating in the machine direction a bonded nonwoven web of multipolymer fibers.
Figure 4:
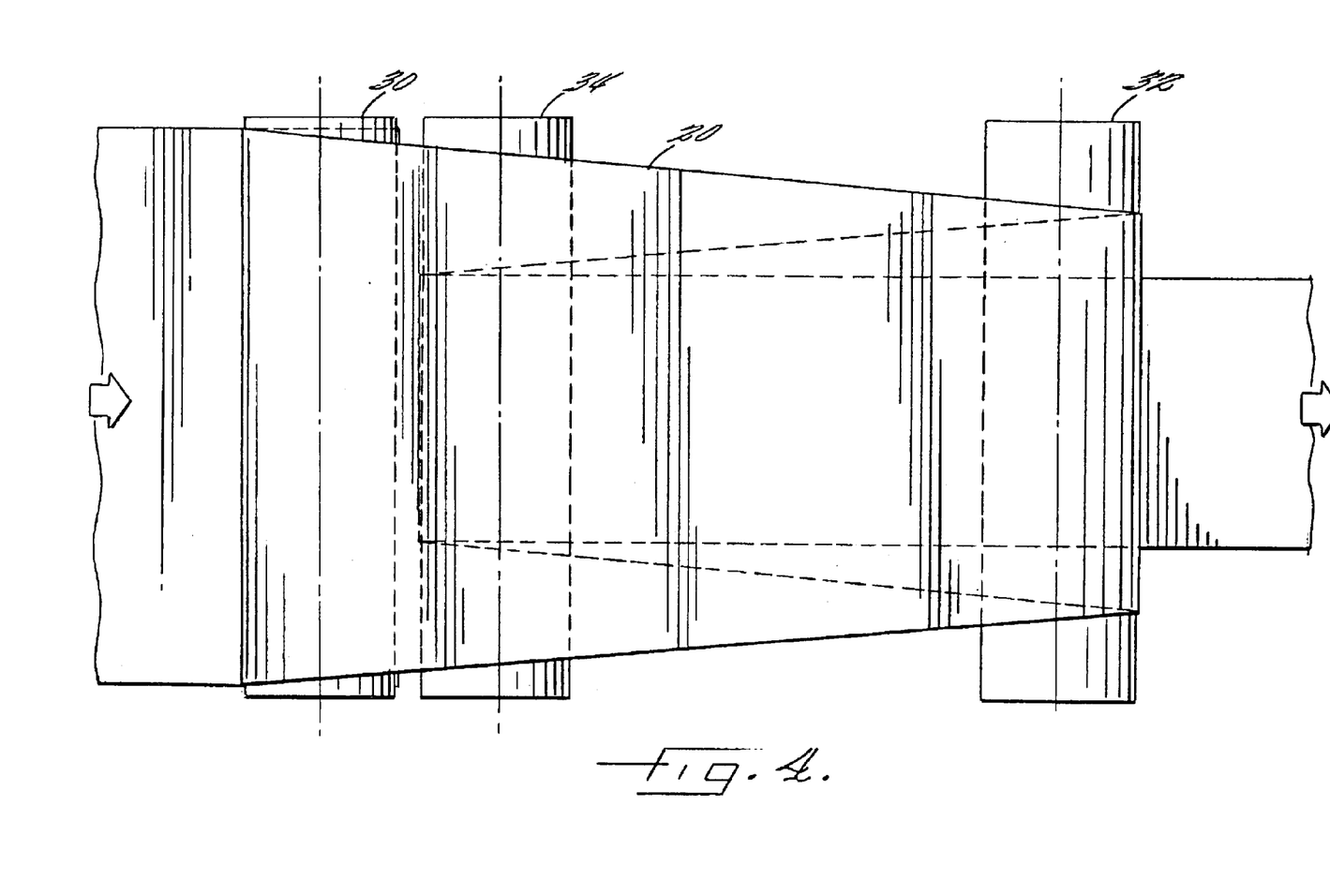
FIG. 4 is a partially broken away top perspective view of a portion of the schematic of FIG. 3 taken along line 4—4 and showing the reduction in the cross direction of the width of the web as the web is stretched.

Typically, the web is stretched in the machine direction. One method of machine direction stretching is schematically represented in FIGS. 3 and 4. It should be recognized that other methods and apparatus can be used to stretch the nonwoven web in the machine direction, although not necessarily with equivalent results. For example, the web can be incrementally stretched in the machine direction using intermeshing or interdigitating rollers.

As shown in FIG. 3, a nonwoven web of multipolymer fibers 20 prepared from the polymer combinations discussed above is supplied from a roll 26 called the unwinder. The web passes around three rolls 28, including a load cell and two idler rolls, arranged at the corners of a triangle for sensing and adjustment of web tension prior to stretching the web. The web is stretched by passing through a series of rolls in three successive S-wrap stations 30, 32, and 34. In each of the S-wrap stations shown, the bottom roller 36, 38, 40 is driven and the top roller and bottom roller form a nip 42, 44, 46 that applies light pressure to the web that does not bond the web, but provides sufficient grip that the web can be stretched between the subsequent sets of S-wrap rollers. Subsequent S-wrap roll stations are driven at increasing speeds to apply increasing tension to the web between each set of rollers in the S-wrap station sufficient to stretch the web.

FIG. 4 represents a partially broken away top perspective view of a portion of the schematic of FIG. 3 taken along line 4—4. The reduction in the cross direction of the width of the web is shown as the web is stretched in the machine direction, first as the web passes between the first and second S-wrap stations 30, 32, and second as the web passes between the second and third S-wrap stations 32, 34. The width of the web is the cross machine direction is considerably reduced between the first S-wrap station and the third. The web is permanently elongated.

It should be recognized that the filaments in the outer portions of the web tend to be elongated faster than the filaments located in the center of the web. For this reason, the distance between the first S-wrap station and the second should be sufficient to provide that the filaments in the center of the web are also permanently elongated to the desired extent.

It should be recognized that other configurations of rollers can be used to stretch the web in the machine direction. Rollers can be used in the omega configuration to apply sufficient tension to the web to permanently elongate the web.

After stretching, the now permanently elongated web is treated in a manner believed to be known to the skilled artisan to improve its uniformity by passing over first and second bow rolls 48, 50 to flatten the web and take out wrinkles. The web is then lightly bonded to stabilize the web against retraction prior to tension adjustment 57 and rolling the web on a winder 58 for supply to a line for making disposable absorbent articles. The web can be bonded by passing through a calender nip 52 formed between two rollers 54, 56. The calender nip should be operated at light pressure and low heat.

The calender preferably is operated so as to take up the web at a lower speed than it is supplied by the third S-wrap station 34. Operating the calender at a lower speed than the third S-wrap station gives the filaments, which have been overstretched to some extent, an opportunity to retract slightly so that they do not retract against the light bond that is later applied. Alternatively, the lamination line could be in line, in which case bonding the web may no longer be necessary.

Table 1 below shows two examples of nonwoven webs prepared in accordance with the invention and compares these webs with a the nonwoven web prior to stretching. The unstretched web is labelled "Control" in Table 1. The nonwoven control web and the two examples were all prepared from spunbond continuous filaments prepared from a blend of a dominant phase of isotactic polypropylene, a dispersed phase of linear low density polyethylene, and Catalloy™ polymer.

quadruples, indicating the high degree to which the web can be stretched in the cross direction, far exceeding the cross machine width of the web prior to stretching. Stretchability in the cross direction is also reflected by the increase in the ratio of the cross direction elongation at peak load to that of the machine direction of about 10 times.

Similar, but opposite, values are obtained in the machine direction. Tensile strength in the machine direction quadruples and elongation at peak load is reduced by about half, indicating that the web is permanently elongated in the machine direction. The properties of the fabric are no longer square.

Table 2, below, compares the extensibility of the control fabric of Table 1 with that of Example 1, Table 1. The force required to extend the web is determined at three different elongations. The control fabric requires a force of 420 grams per inch to elongate the fabric 100%. At 200 and 350% elongation, the control web breaks. In contrast, the web of Example 1 requires a force of only 260 grams per inch to elongate the web by 350%.

TABLE 1

| Example | | Basis Wt. g/m² | CD tensile strength (g/in) | CD Elongation at peak load (%) | MD tensile strength (g/in) | MD Elongation at peak load (%) | MD/CD Tensile Ratio | MD/CD Elongation Ratio | CD/MD Tensile Ratio | CD/MD Elongation Ratio |
|---|---|---|---|---|---|---|---|---|---|---|
| Control | Avg. | 25.063 | 908 | 184.2 | 2562 | 191.5 | 2.82 | 1.04 | 0.35 | 0.96 |
| | S.D. | 0.875 | 132.5719 | 25.8 | 351.4531 | 15.1 | | | | |
| Ex. 1 | Avg. | 62.07 | 498.67 | 750.70 | 8135.83 | 70.01 | 16.32 | 0.09 | 0.06 | 10.72 |
| | S.D. | 3.22 | 77.71 | 98.26 | 1250.15 | 27.02 | | | | |
| | % Change | 148% | −45% | 308% | 218% | −63% | 478% | −91% | −83% | 1015% |
| Ex. 2 | Avg. | 64.61 | 517.53 | 707.35 | 8512.37 | 77.25 | 16.45 | 0.11 | 0.06 | 9.16 |
| | S.D. | 3.51 | 69.23 | 83.60 | 1075.78 | 29.67 | | | | |
| | % Change | 158% | −43% | 284% | 232% | −60% | 483% | −89% | −83% | 852% |

Examples 1 and 2 are were both prepared from the same control fabric at different line conditions. The relatively slight differences in the values obtained for the physical characteristics of these webs is due primarily to differences in line conditions.

The control fabric had similar physical characteristics in the machine direction as in the cross machine direction, as is reflected by the ratio of the tensile strength in the machine direction to the tensile strength in the cross direction of 2.82. A value of 2.82 means that the nonwoven control web was relatively square in its properties. The balance of properties is also reflected by the MD/CD elongation ratio, which reflects that the fabric is stretchable and permanently elongatable in either the cross direction or the machine direction.

Permanent elongation of the control fabric in the machine direction produced nonwoven webs having the characteristics recited in Table 1 for Examples 1 and 2. The basis weight more than doubled from about 25 g/m² to over 60 g/m². The increase in basis weight reflects that the dimension of the fabric in the cross direction is greatly reduce by stretching in the machine direction.

Tensile strength in the cross direction, CD, in g/in, which is grams per one inch strip of material, is reduced by nearly half. Elongation at peak load in the cross direction, as a percentage based on the original width of the web,

TABLE 2

| Example | Load at 100% el. (g/in) | Load at 200% el. (g/in) | Load at 350% el. (g/in) |
|---|---|---|---|
| Control | 420 | Breaks | Breaks |
| Example 1 | 52 | 109 | 260 |

Figure 5:
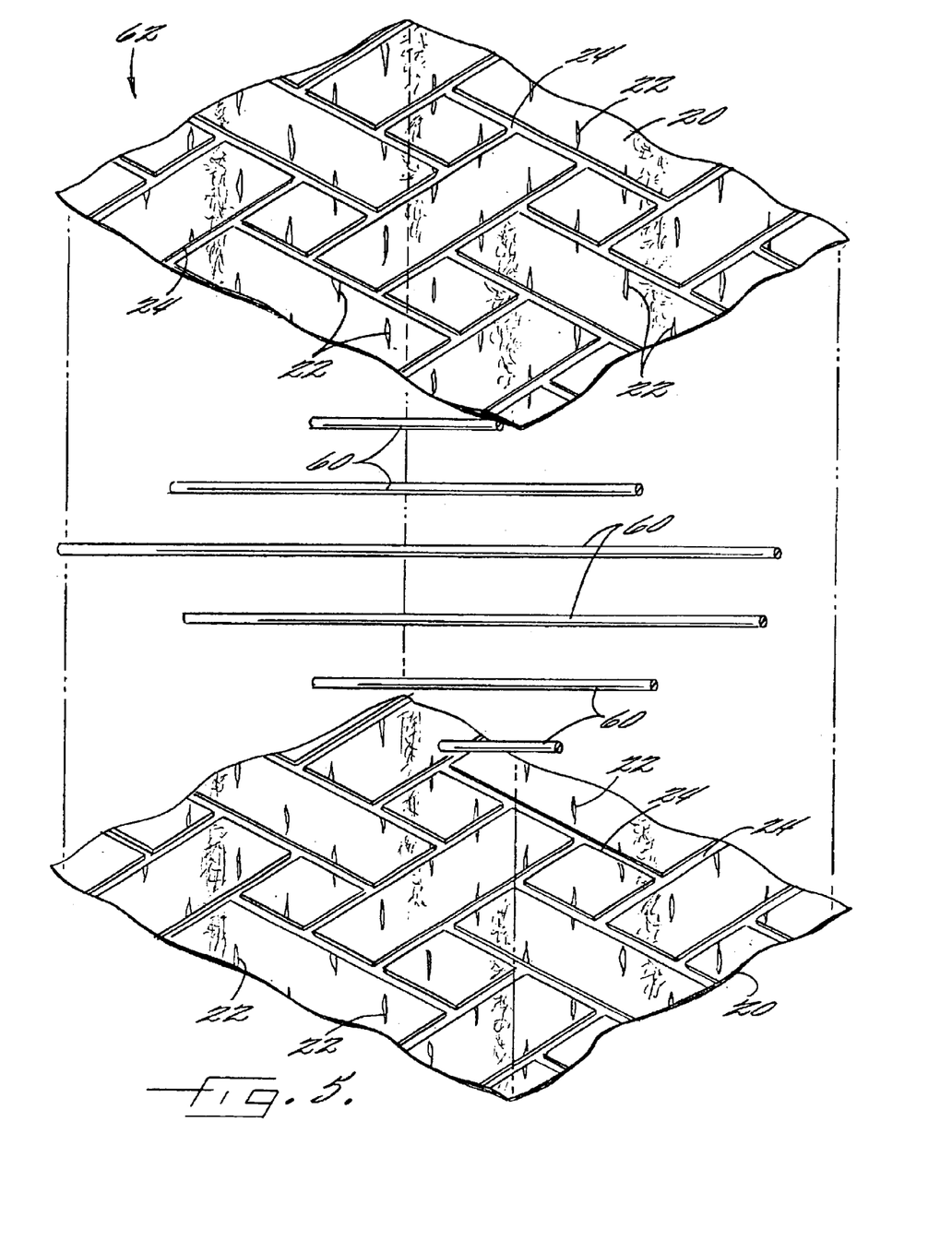
FIG. 5 is an exploded perspective view of a laminate of two nonwoven webs of the invention as shown in FIG. 2 with elastomeric strands placed between the two webs.

A nonwoven web stretched as shown in FIGS. 3 and 4 is illustrated in FIG. 5 in an exploded view of an elastic fabric laminate of the invention 62. Elastomeric strands 60 are placed between two nonwoven webs 20 (FIG. 2) and the laminate is bonded, normally by application of a hot melt or other suitable adhesive. It should be recognized that the laminate can be prepared with a single nonwoven web on one side to produce a two layer laminate rather than a three layer laminate, if desired. The fabric of the invention has sufficient cover provided by Z axis development to preclude substantial glue bleed-through. The elastomeric strands are oriented to stretch in a direction perpendicular to the direction in which the nonwoven webs were permanently elongated. The webs were stretched in the machine direction as shown in FIGS. 3 and 4, and so the elastomeric fibers are oriented to stretch in the cross machine direction.

The fabric laminate is elastic in the cross machine direction and recovers substantially all of the distance it is stretched when stretched below the elastic limit of the elastomeric strands. The nonwoven webs of the invention can stretch in the cross machine direction to many times the distance of the initial width of the nonwoven web prior to elongation. Typically, the strands are bonded to the web directly, without being placed under tension or elongated.

If it is desired that the fabric laminate stretch in two directions, then the elastic component that is sandwiched between the nonwoven webs of the invention should provide for stretch in two directions. The nonwoven web can then be applied to the elastic component so as to form gathers when the elastic component is relaxed that can allow stretch in the direction in which the web was permanently elongated. For example, the web can be applied to tensioned elastomeric strands so that the gathers form when the strands are relaxed. The laminate can then be stretched and will exhibit recovery to the extent allowed by the gathers.

A wide variety of elastic components are suitable for use in the practice of the invention. Elastomeric strands, scrim, or elastomeric film, including perforated and nonperforated films and barrier or moisture vapor transmitting films, are all suitable for use, depending on the results desired. Elastomeric strands and scrim tend to produce fabrics with enhanced breathability as compared to films and are preferred in countries of high heat and humidity. Films are preferred in more arid climates since they are cheaper.

The elastic laminate of the invention is suitable for use as an elastic fabric having highly desirable cloth like characteristics. The laminate is suitable for use in a variety of disposable absorbent articles. The laminate is useful as a stretch side panel in diaper construction.

Figure 6:
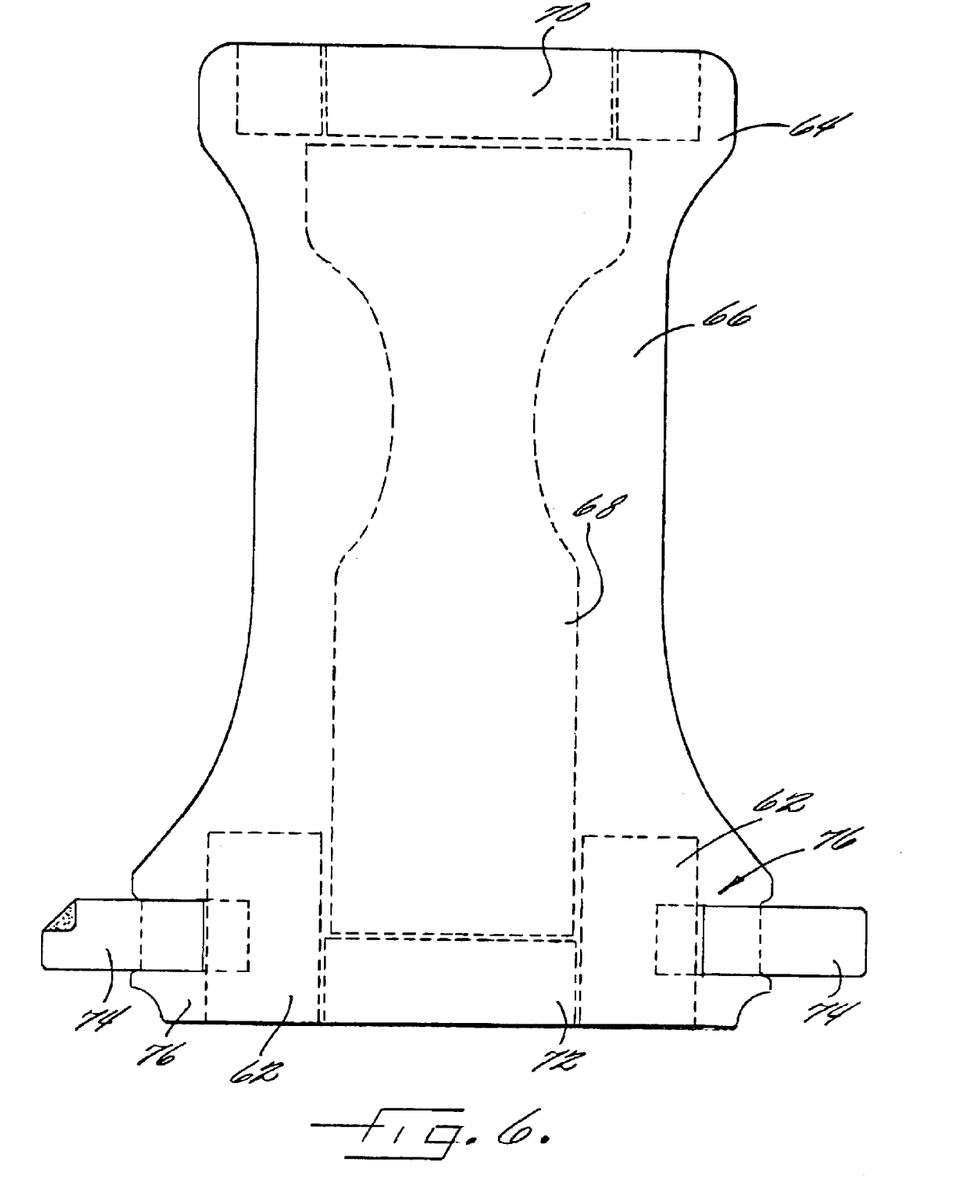
FIG. 6 is a plan view of the relevant structure of a disposable diaper of the invention having the outer surface back sheet facing the viewer.

A disposable diaper 64 is represented in FIG. 6 that incorporates a pair of elastic side panels 62 made from fabric laminate of the invention. The diaper is shown in plan view having the outer surface back sheet 66 facing the viewer. Internal structure is shown in outline by the dashed lines. The diaper includes a water pervious topsheet 65 (FIG. 7), a water impervious back sheet 66, and an absorbent core 68 that typically comprises wood pulp or other absorbent material and typically includes superabsorbent polymer powder. A surge layer, not shown, may be used to provide a holding area for urine in the front waist region for the time required for the superabsorbent polymer to take up the urine after strikethrough.

The diaper includes front and rear waist bands 70, 72, which typically are elasticized. Securing tabs 74 are provided on the back waist region on opposite sides of the waistband for securing the diaper back waist region to the front waist region about the waist of the wearer. The securing tabs typically are secured to a landing panel on the front waist region that includes decorative indicia. The tabs can be secured by pressure sensitive adhesive or a hook and loop fastening system similar to Velcro.

The front and rear waist regions are shown to flare outwardly from the body of the diaper to provide sufficient material to encircle the waist and to provide for secure attachment of the back waist region to the front about the waist of the wearer. These outwardly flared portions are often referred to as ears. The securing tabs extend outwardly from and are anchored to the ears 76 of the back waist region.

The elastic side panels of the invention 62 are laminated into the diaper structure between the back sheet and the topsheet. As shown, the anchored ends of the securing tabs overlap somewhat the elastic side panels. The side panels are oriented in the diaper to provide transverse stretch, which is in the direction of tension on the securing tab, to improve the fit of the diaper, even under conditions where the wearer is active. When made with elastic scrim or elastomeric fibers, the composite typically has good breathability, but also contributes to fluid barrier outside the strikethrough and absorbent region. Elastic film can also be used as described in Weil et al. U.S. Pat. No. 5,242,436, which illustrates a diaper construction having an elastic side panel therein.

Figure 7:
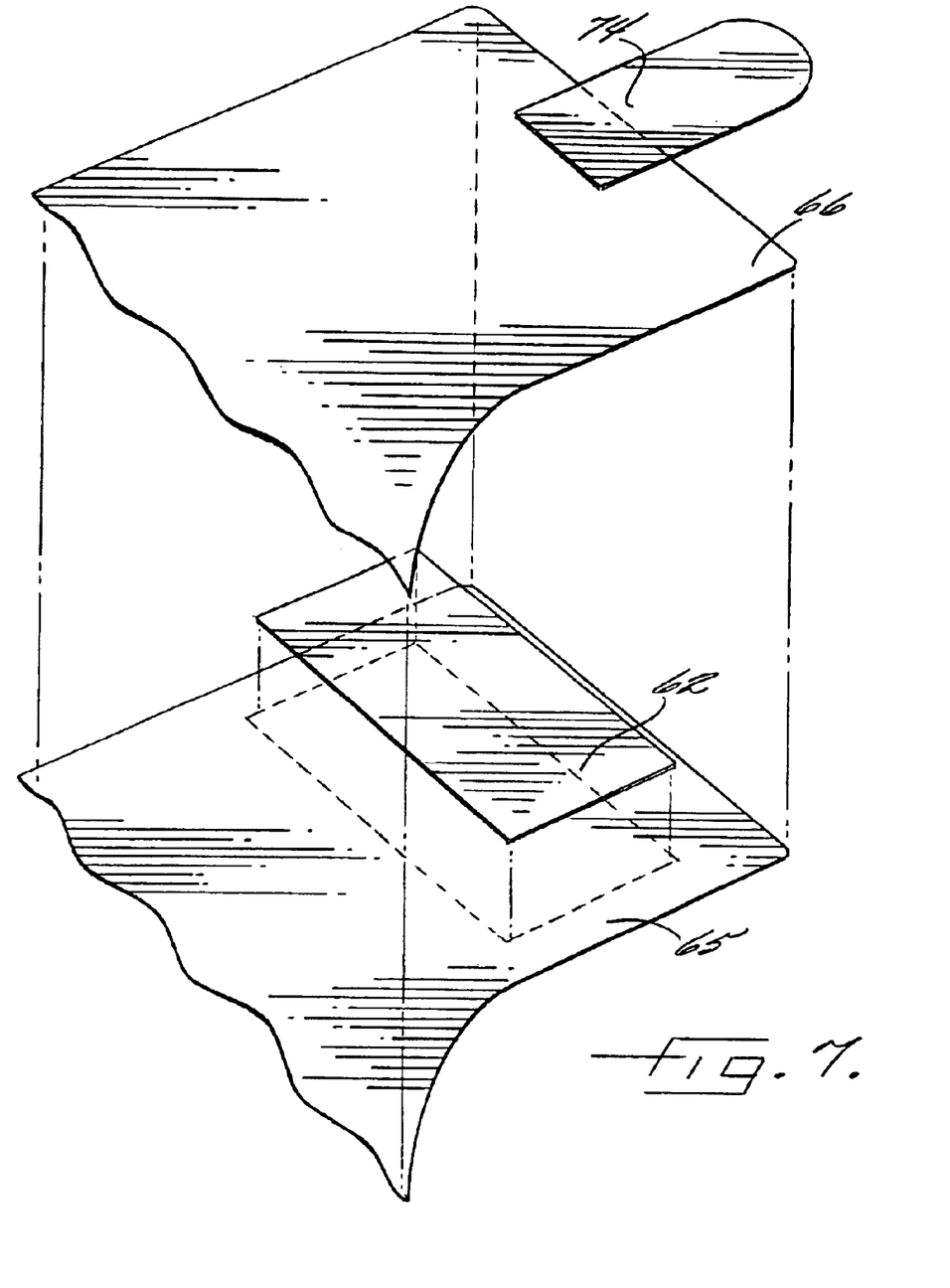
FIG. 7 is an exploded perspective view of a broken away portion of the diaper of FIG. 6, showing the placement within the diaper of a composite fabric of the invention.

Placement of the elastic side panel of the invention into the diaper is represented in FIG. 7. As shown, the laminate is placed between the top sheet and the back sheet so as to provide some elasticity to the ear region in the direction of pull of the securing tab.

One of the advantages of the invention is that the fabric of the invention provides a soft, cloth like hand and excellent cover, and yet is exceptionally strong. In the diaper construction illustrated, the topsheet and the back sheet typically are constructed of inelastic materials that do not exhibit stretch and recovery and it normally is necessary to treat the diaper construction in the region of the elastic side panel so that the topsheet and back sheet will be activated to move with the elastic side panel. A suitable method for mechanically incrementally stretching in the cross direction the composite of the top sheet, elastic stretch laminate of the invention, and the back sheet is described in Weil et al. U.S. Pat. No. 5,242,436.

The description of the method of U.S. Pat. No. 5,242,436 is incorporated herein by reference in its entirety. The composite passes through meshing corrugated rolls as described. Incremental stretching in the cross direction permanently elongates the topsheet and back sheet components and destroys any light bonding of the elastomeric nonwoven web composite. The topsheet and the back sheet can now be stretched to provide for stretching of the elasticized side panel. The fabric of the invention from which the elasticized side panel is made is sufficiently strong by virtue of having been already stretched in the machine direction to withstand the rigors of incremental stretching in the composite and to provide a desirable provide cover.

It should be recognized that the nonwoven fabric laminate of the invention can be used in the manner described in U.S. Pat. Nos. 4,981,747 and 5,114,781 as a fabric that is secured to the securing tab and mounted onto the diaper back sheet rather than laminated within the diaper between the topsheet and the back sheet.

Particular embodiments of the invention have been described in detail in the drawings, photomicrographs, and specification and specific terms have been used. These should be understood in a generic and descriptive sense and not for purposes of limitation. The scope of the invention is defined by the claims.

What is claimed is:

1. A nonwoven web formed of highly elongatable multi-polymer fibers, said fibers being substantially oriented in one direction, and said web having a plurality of discrete point bond sites throughout the web bonding the fibers together, said point bond sites comprising areas where the fibers have been fusion bonded together to form bond sites, said bond sites being imbedded within the web between opposite surfaces of the web and of a distorted, non-planar configuration extended generally in the Z-axis direction of the web, and said web having an extensibility in one direction of at least 100 percent when a load of 300 grams force per inch or less is applied in said one direction, and wherein the ratio of the tensile strength of the web in the direction of orientation of the fibers to the tensile strength in the direction transverse to the direction of orientation is at least about 10:1.

2. The web of claim 1 wherein the ratio of the tensile strength of the web in the direction of orientation of the fibers to the tensile strength of the web in the other direction is at least about 16:1.

3. The web of claim 1 wherein the ratio of the elongation at peak load of the web in the direction transverse to the direction of orientation of the fibers to the elongation at peak load in the direction of elongation is at least about 6:1.

4. The nonwoven web of claim 1 wherein the extensibility of the web in said one direction is at least 200 percent.

5. The nonwoven web of claim 1 wherein the extendibility of the web in said one direction is at least 350 percent.

6. The nonwoven web of claim 1 wherein said elongation at peak load is at least about 500%.

7. The web of claim 1 additionally including, in addition to said plurality of distorted non-planar bond sites, a second plurality of bond sites that are generally planar extend parallel to the surface of the web.

8. The nonwoven web of claim 1 wherein said multipolymer fibers comprise a blend of polypropylene and polyethylene.

9. The nonwoven web of claim 1 wherein said multipolymer fibers comprise a blend of two immiscible polymer phases and a third component which is at least partially miscible with the two immiscible polymer phases.

10. A nonwoven web formed of highly elongatable multipolymer fibers, said fibers being substantially oriented in one direction, said multipolymer fibers being formed from a blend comprising:
   a) isotactic polypropylene present in an amount of from about 65 to 80 percent by weight based upon the weight of said blend;
   b) linear low density polyethylene present in an amount of from about 1 to 5 percent by weight based upon the weight of said blend; and
   c) a block or grafted polyolefin copolymer or terpolymer having at least a portion of the chain thereof miscible with said isotactic polypropylene and wherein said block or grafted polyolefin copolymer or terpolymer is present in an amount of from about 15 to 30 percent by weight based upon the weight of said blend, said web having a plurality of discrete point bond sites throughout the web bonding the fibers together, said point bond sites comprising areas where the fibers have been fusion bonded together to form bond sites, said bond sites being imbedded within the web between opposite surfaces of the web and of a distorted, non-planar configuration extending generally in the z-axis direction of the web, said web having an extensibility in one direction of at least 300 percent when a load of 300 grams force per inch or less is applied in said one direction, and wherein the ratio of the tensile strength of the web in the direction of orientation of the fibers to the tensile strength in the direction transverse to the direction of orientation is at least about 10:1.

11. The nonwoven web of claim 10 wherein the multi-component fibers are selected from the group consisting of spunbond continuous filaments, carded discontinuous staple fibers, and meltblown fibers.

12. A bonded nonwoven web of multipolymer fibers, said nonwoven web having discrete bond sites throughout the web bonding the fibers together, said bond sites comprising a first plurality of bond sites where the fibers have been fusion bonded together and the bond sites are of a distorted, non-planar configuration extending generally in the z-axis direction of the web, and said web additionally including a second plurality of second bond sites that are generally planar and extend parallel to the surface of the web.

13. The nonwoven web of claim 12, wherein the web has an elongation at peak load in one or the other of the machine or cross machine directions of at least about 400% and a ratio of elongation at peak load in said one direction to the elongation at peak load in said other direction of at least about 6:1.

14. The nonwoven web of claim 13 wherein said elongation at peak load is at least about 500%.

15. The nonwoven web of claim 12 wherein said ratio of elongation at peak load in said one direction to the elongation at peak load in said other direction is at least about 8:1.

16. The web of claim 12 wherein said web is a cold stretched web.

17. A nonwoven web comprising a plurality of spunbond continuous filaments formed of a blend of two immiscible polymer phases and a third component which is at least partially miscible with the two immiscible polymer phases, said web having a plurality of discrete point bond sites throughout the web bonding the continuous filaments together, said web having an extensibility in one direction of at least 70 percent when a load of less than or equal to 300 grams per inch is applied to said web in said one direction.

18. The web of claim 17 wherein said extensibility is at least 100 percent.

19. The web of claim 17 wherein said extensibility is at least 200 percent.

20. The web of claim 17 wherein said extensibility is at least 350 percent.

* * * * *

UNITED STATES PATENT AND TRADEMARK OFFICE
CERTIFICATE OF CORRECTION

| | | |
|---|---|---|
| PATENT NO. | : 6,849,324 B2 | Page 1 of 1 |
| APPLICATION NO. | : 09/949108 | |
| DATED | : February 1, 2005 | |
| INVENTOR(S) | : Meece et al. | |

It is certified that error appears in the above-identified patent and that said Letters Patent is hereby corrected as shown below:

Title page, Item (54) and Column 1, line 1,

In the title, "UNDIRECTIONALLY" should read --UNIDIRECTIONALLY--.

Signed and Sealed this

Fourteenth Day of October, 2008

JON W. DUDAS
*Director of the United States Patent and Trademark Office*